United States Patent [19]

Malpass et al.

[11] Patent Number: 4,547,477

[45] Date of Patent: Oct. 15, 1985

[54] ORGANOMAGNESIUM SOLUTIONS OF LOW VISCOSITY

[75] Inventors: Dennis B. Malpass, LaPorte; Dale W. Webb, Pasadena, both of Tex.

[73] Assignee: Texas Alkyls, Inc., Deer Park, Tex.

[21] Appl. No.: 591,717

[22] Filed: Mar. 21, 1984

[51] Int. Cl.$^4$ .................. B01J 31/12; C07F 3/02; C08F 4/62
[52] U.S. Cl. .................. 502/153; 502/152; 502/156; 526/124; 526/151; 528/413; 585/452
[58] Field of Search .................. 502/152–154, 502/156, 133

[56] References Cited

U.S. PATENT DOCUMENTS

| | | | |
|---|---|---|---|
| 3,737,393 | 6/1973 | De Vries | 502/153 |
| 4,426,316 | 1/1984 | Gessell | 502/169 |
| 4,456,547 | 6/1984 | Fuentes, Jr. | 502/117 |

FOREIGN PATENT DOCUMENTS 0044665  1/1982  European Pat. Off. ............ 502/152

*Primary Examiner*—P. E. Konopka
*Attorney, Agent, or Firm*—Joel G. Ackerman

[57] ABSTRACT

The viscosity of hydrocarbon solutions of dialkylmagnesium compounds are reduced by using a reducing agent comprising a defined benzene derivative, a substance produced by reacting such a benzene derivative with magnesium or a dialkylmagnesium compound or a mixture of one of the foregoing with an organoaluminum viscosity reducing agent.

11 Claims, No Drawings

ORGANOMAGNESIUM SOLUTIONS OF LOW VISCOSITY

Organomagnesium compounds are known to be useful in a wide variety of chemical reactions. As reagents, organomagnesium compounds are used for the reduction of ketones, the metalation of aromatic compounds, and the alkylation of metal halides or oxides. As catalysts, organomagnesium compounds are useful in the dimerization and polymerization of olefins, see British Pat. No. 1,251,177; the polymerization of epoxides, see U.S. Pat. No. 3,444,102; and the preparation of telomers, see U.S. Pat. No. 3,742,077. While they perform many of the functions performed by Grignard reagents, organomagnesium compounds, owing to differences in electronic and steric factors, are more reactive toward certain types of compounds. See also U.S. Pat. Nos. 3,646,231 and 3,822,219.

Some of the most useful organomagnesium compounds are dialkylmagnesium compounds. Although some are insoluble in hydrocarbon solvents, it has been shown that those containing branched-chain alkyl groups, cyclic alkyl groups, or straight-chain groups of five carbon atoms or more are indeed soluble. Examples include di-tert-butylmagnesium, di-sec-butylmagnesium, di-n-amylmagnesium, methylisobutylmagnesium, ethylisobutylmagnesium, di-n-hexylmagnesium, etc. In addition, certain combinations of straight-chain lower alkyl groups have also been found to be soluble—n-butylethylmagnesium, n-butylmethylmagnesium, and n-propylmethylmagnesium. Such compositions are disclosed, for instance, in U.S. Pat. Nos. 4,207,207 and 4,222,969.

Unfortunately, most of the resulting solutions are highly viscous. Exceptions are solutions of branched-chain dibutylmagnesium compounds such as di-sec-butylmagnesium or mixed dibutyl compounds such as n-butyl-sec-butyl magnesium. This detracts from the utility of the compounds since their viscosity renders them less reactive as reagents and catalysts and more difficult to handle and transfer. In addition, the viscosity of the solutions makes it difficult to prepare the compounds in a form free of halides and other undesirable solids. Following the procedures described in Glaze and Selman, *Journal of Organometallic Chemistry*, Vol. 5, p. 477, (1967), and W. N. Smith, *Journal of Organometallic Chemistry*, Vol. 64, p. 25 (1974), dialkylmagnesium compounds are conveniently prepared by reaction between metallic magnesium and the appropriate alkyl chloride in the desired hydrocarbon solvent. The by-product of this reaction is magnesium chloride, which is insoluble in hydrocarbons. Both the magnesium chloride and any unreacted magnesium metal, which is frequently used in excess, remain as solid matter suspended in a viscous liquid. The viscosity prevents an easy separation of the solution from the solids, requiring instead centrifuging equipment or the like or a long period for the solids to settle.

A number of different substances have been found effective in reducing the viscosity of such normally viscous solutions of organomagnesium compounds. These substances include, for instance, organometallic compounds of gallium, indium, and lithium (U.S. Pat. No. 4,299,781); chloroaryl solvents (U.S. Pat. No. 3,264,360); and organoaluminum compounds (U.S. Pat. No. 3,737,393).

SUMMARY OF THE INVENTION

This invention comprises a hydrocarbon solution of a dialkylmagnesium compound having reduced viscosity, which solution comprises:
(a) a hydrocarbon solvent;
(b) a dialkylmagnesium compound normally soluble in hydrocarbon solvents; and
(c) an effective viscosity reducing amount of:
  (i) a benzene derivative having the formula

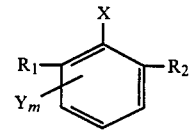

in which X is hydroxy, amino, or mono- or di-lower alkylamino; $R_1$ and $R_2$ are independently phenyl, mono- or polysubstituted phenyl in which the substituents are substantially non-reactive towards magnesium or dialkylmagnesium compounds, or a tertiary alkyl group having the formula

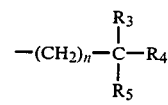

in which n is zero or 1 and $R_3$, $R_4$ and $R_5$ are independently methyl or ethyl; Y is hydrogen or a substituent which is substantially non-reactive towards magnesium and dialkylmagnesium compounds; and m is an integer from 1 to 3;
  (ii) a substance produced by reacting a compound as defined in (i) with magnesium or a dialkylmagnesium compound; or
  (iii) a mixture of a substance as defined in (i) or (ii) with an organoaluminum viscosity reducing agent.

DETAILED DESCRIPTION OF THE INVENTION

The present invention pertains to low viscosity solutions of organomagnesium compounds in hydrocarbon solvents.

The term "hydrocarbon solvent" is used to designate aliphatic, cycloaliphatic and aromatic hydrocarbons. Illustrative of aliphatic solvents are n-pentane, isopentane, n-hexane, n-heptane, n-octane, isooctane, pentamethylheptane, and gasoline and other petroleum fractions. Illustrative of cycloaliphatic solvents are cyclohexane, methylcyclohexane, methylcyclopentane, cycloheptane, and cyclooctane. Illustrative of aromatic solvents are benzene, toluene, xylenes, ethylbenzene, tetralin, and α-methylnaphthalene. Preferred solvents are those containing 5 to 20 carbon atoms, inclusive. More preferred are those containing 6 to 15 carbon atoms, inclusive. Particularly preferred solvents are those which have boiling points between about 69° C. and about 110° C.

The dialkylmagnesium compound is one which is normally soluble in such hydrocarbon solvents, but which also normally forms viscous solutions therein. Illustrative of such dialkylmagnesium compounds are butylmethylmagnesium, butylethylmagnesium, butyloctylmagnesium, di-n-amylmagnesium, diisoamylmagnesium, di-n-hexylmagnesium, di-n-octylmagnesium, and in general, dialkylmagnesium compounds in which the alkyl groups have 5 or more carbon atoms each, preferably 5 to 20 carbon atoms, and most preferably 5 to 12 carbon atoms. Also included in such dialkylmagnesium compounds are mixtures of two or more dialkylmagnesium compounds such as diisoamyl plus diethylmagnesium, or butylethylmagnesium plus di-n-hexylmagnesium.

The concentration of the dialkylmagnesium or mixture of dialkylmagnesium compounds in the solvent is not critical, and may vary over a wide range. In general, however, compositions according to this invention will contain one or more dialkylmagnesium compounds in an amount of from about 5 to about 60 weight percent of the overall composition, preferably from about 10 to about 30 weight percent.

The viscosity reducing agents which have been found effective according to this invention can be generally characterized as comprising a series of sterically hindered phenols, anilines, and N-(mono- or di-lower alkyl) anilines and are generally defined by the formula

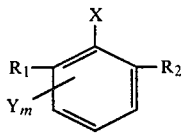

In this formula, X is hydroxy, amino, or mono- or di-lower alkylamino, $R_1$ and $R_2$ are independently phenyl, substituted phenyl in which the substituents are substantially non-reactive towards magnesium or dialkylmagnesium compounds, or a tertiary alkyl group having the formula

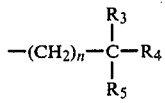

in which n is 0 or 1 and $R_3$, $R_4$ and $R_5$ are independently methyl or ethyl; Y is hydrogen or a substituent which is substantially non-reactive towards magnesium or dialkylmagnesium compounds, and m is an integer from 1 to 3.

Examples of tertiary alkyl groups included in such compounds are tertiary butyl (n=0, $R_3$-$R_5$=methyl), neopentyl (n=1, $R_3$-$R_5$=methyl), tertiary amyl (n=0, $R_3$ and $R_5$=methyl, $R_4$=ethyl), neohexyl (n=1, $R_3$ and $R_5$=methyl, $R_4$=ethyl), and 1-methyl-1-ethylpropyl (n=0, $R_3$=methyl, $R_4$ and $R_5$=ethyl).

The benzene derivatives may have substituents only at the 1-, 2- and 6-positions (corresponding to groups X, $R_1$ and $R_2$) or may additionally have substituents at other positions on the phenyl ring (groups $Y_m$). The additional substituents ($Y_m$) should be non-reactive with magnesium or dialkylmagnesium compounds, so that undesired side products are not formed in this composition, and may be, for instance, lower alkyl or lower alkoxy. The terms "lower alkyl" and "lower alkoxy" are intended to include such straight- and branched-chain groups having from 1–6 carbon atoms, preferably 1–4 carbon atoms. Similar limitations apply to any substituents on phenyl rings located at the $R_1$ or $R_2$ position in these compounds.

The viscosity reducing agent defined by the formula above may be introduced per se, or alternatively may be introduced in a form which has already been reacted with magnesium or with a dialkylmagnesium compound to produce a corresponding magnesium phenoxide, anilide or N-mono- or dialkyl anilide.

The viscosity reducing agents defined above may be utilized along, but for purposes of efficiency are preferably utilized in a mixture with an organoaluminum viscosity reducing agent. Such substances are disclosed, for instance, in U.S. Pat. Nos. 3,737,393 and 4,127,506, and include: trialkylaluminum compounds such as trimethyl-, triethyl- and tri-n-hexylaluminum; mono- or dialkylaluminum halides such as diethylaluminum chloride or ethylaluminum dichloride; dialkylaluminum hydrides such as diisobutylaluminum hydride; aluminum alkoxides such as triisopropoxy aluminum; and aluminum halides, such as aluminum trichloride, which will react with the alkyl halide used to produce the dialkylmagnesium, forming one or more of the above types of organoaluminum compounds. In such mixtures, the mole ratio of the benzene derivative (phenol, aniline or alkylaniline) to trialkylaluminum will preferably range from about 0.5:1 to about 2:1.

The invention is further illustrated by the following examples.

EXAMPLE 1

A solution of 8.0 weight percent n-butylethylmagnesium in heptane was prepared by the following procedure.

A reactor was charged, under a nitrogen atmosphere, with n-heptane, magnesium powder and previously prepared solution of n-butylethylmagnesium in n-heptane (to assist in initiating the reaction). The contents were heated to 100° C., and part of an equimolar mixture of n-butyl and ethyl chlorides added. After a temperature rise indicated the reaction had started, the remaining mixture was added in increments until all had been charged. The resulting slurry was allowed to settle for 2 days at 100° C., then the clear supernatant liquid was transferred to tared sample bottles. The viscosity was measured at 35° C. and found to be 1387 centipoise.

To a bottle containing 30.0 g of the solution (0.531 g Mg, 0.0218 mole) was added 0.0514 g (0.233 millimole) of 2,6-di-tertiarybutyl-4-methylphenol (commonly known as butylated hydroxy toluene or BHT), also dissolved in heptane. The viscosity of the resulting solution was measured at 35° C. and found to be only 209 centipoise. The molar ratio of magnesium/BHT in this solution was 94:1.

EXAMPLE 2

A solution of 10 weight percent n-butylethylmagnesium in heptane was prepared as in Example 1. Analysis indicated the product was not equimolar in n-butyl and ethyl, so additional n-butyl chloride was charged. The resulting slurry was allowed to settle for 6 days at 100° C., then the clear supernatant liquid was transferred to tared sample bottles. The viscosity was measured at 35° C. and found to be 854 centipoise.

To the bottles of this solution there were added solutions of test compounds variously dissolved in heptane or toluene. The amount of solvent utilized varied with the test compound, but was as little as possible so as to avoid adding excessive solvent to the n-butylethylmagnesium solution. The later solution was heated at 65° C. for ½ hour before addition of the test compounds. The test compounds were added using a small syringe for accurate weighings and the bottles of solution vigorously shaken, then reheated at 65° C. for another ½ hour. If a test compound caused a great reduction in viscosity the reheating was eliminated. This series of tests was done in three phases. Viscosities of the resulting solutions were all measured at 35° C. The results are given below in Table I. Control experiments were also conducted in which an amount of heptane or toluene, respectively, corresponding roughly to the amount introduced as a solvent for the test compounds was added alone, with no test compound present. The heptane was about 3.6 weight percent of the solution while the toluene was about 10 weight percent. The viscosities of these resulting solutions were measured, and are also contained in Table I.

The compounds which were tested and found to be effective viscosity reduction agents correspond to the formula

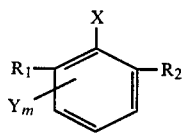

and were as follows.

| Test Cmpd. No. | X | $R_1$ | $R_2$ | $Y_m$ | Name |
|---|---|---|---|---|---|
| 1 | OH | t-$C_4H_9$ | t-$C_4H_9$ | H | 2,6-di-tert-butylphenol |
| 2 | OH | t-$C_4H_9$ | t-$C_4H_9$ | 4-$CH_3$ | 2,6-di-tert-butyl-4-methylphenol |
| 3 | OH | $C_6H_5$ | $C_6H_5$ | H | 2,6-diphenylphenol |
| 4 | $NH_2$ | t-$C_4H_9$ | t-$C_4H_9$ | 4-t-$C_4H_9$ | 2,4,6-tri-tert-butyl aniline |

TABLE I

| Test Compound | | Solvent | Mole, Ratio, Mg/Test Cmpd. | Viscosity, Centipoise (at 35° C.) |
|---|---|---|---|---|
| No. | meq$^a$ | | | |
| — | — | — | — | 854$^c$ |
| — | — | heptane$^b$ | — | 682 |
| 2 | 5.0 | heptane | 202 | 465 |
|   | 9.4 | heptane | 106 | 379 |
|   | 21 | heptane | 48 | 253 |
|   | 103 | heptane | 9.7 | 61 |
| — | — | — | — | 775$^d$ |
| — | — | toluene$^b$ | — | 579 |
| 1 | 10 | heptane | 100 | 329 |
|   | 16 | heptane | 63 | 302 |
|   | 103 | heptane | 9.7 | 55 |
| 2 | 14 | toluene | 73 | 383 |
|   | 21 | toluene | 47 | 234 |
|   | 117 | toluene | 8.5 | 51 |
| 3 | 12 | toluene | 85 | 357 |
|   | 16 | toluene | 62 | 332 |
|   | 106 | toluene | 9.4 | 7 |
| — | — | — | — | 602$^e$ |
| 4 | 12 | heptane | 82 | 791 |
|   | 18 | heptane | 56 | 585 |
|   | 106 | heptane | 9.6 | 9 |

$^a$Milliequivalents per mole of magnesium.
$^b$Controls - solvent added without any test compound.
$^c$Original measurement - for first phase of tests.
$^d$Second measurement - for second phase of tests.
$^e$Third measurement - for third phase of tests. This value is thought to be incorrectly low due to contamination during measurement.

EXAMPLE 3

A solution was prepared containing 9.0 weight percent n-butylethylmagnesium in heptane. This solution took the form of a slurry due to unreacted magnesium metal and by-product magnesium chloride that were not separated as in the previous examples.

To a sample bottle containing about 155 milliliters of the slurry was added 0.2611 g (1.185 millimole) of Test Compound 1 as a heptane solution, such that the molar ratio of magnesium/test compound was about 69. There was then added 0.2950 g (1.044 millimole) of tri-n-hexylaluminum to give a molar ratio of magnesium/aluminum of about 79. The mixture was heated to 60° C. for 30 minutes, then allowed to cool to room temperature. The bottle was shaken to thoroughly mix the solid and liquid portions, then the solids were allowed to settle undisturbed. The rate of settling was measured over a period of 400 minutes by measuring the height (in centimeters) of clear supernatant liquid in the bottle. Observations indicated that after 100 minutes, there was approximately 4.0 cm of clear supernatant liquid, and after 200 minutes, approximately 5.0 cm. The maximum amount of liquid was approximately 5.4 cm, which was reached after 340 minutes.

To the bottle there was then added another 0.0738 g (0.261 millimole) of tri-n-hexylaluminum such that the mole ratio of magnesium/aluminum was about 62. The bottle was shaken and the rate of settling measured as before. The settling occurred somewhat more quickly; after 100 minutes there was approximately 4.6 cm of clear supernatant liquid and approximately 5.4 cm after 200 minutes. The maximum amount of lqiuid was approximately 5.5 cm, which was reached after 250 minutes.

In comparison, the product in Example 1 had to settle at 100° C. for 2 days to get enough clear supernatant liquid to remove for the work that followed. In Example 2, the product had to settle at 100° C. for 6 days in order to get a greater amount of clear supernatant liquid for the work that followed. These differences in settling times illustrate the reduction of viscosity of the n-butylethylmagnesium solution by the combination of BHT (Test Compound 1) and a trialkylaluminum.

What is claimed is:

1. A hydrocarbon solution of a dialkylmagnesium compound having reduced viscosity, which solution comprises:
   (a) a hydrocarbon solvent;
   (b) a dialkylmagnesium compound normally soluble in hydrocarbon solvents; and
   (c) an effective viscosity reducing amount of:
      (i) a benzene derivative having the formula

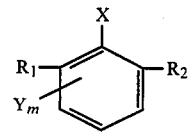

in which X is hydroxy, amino, or mono- or di-lower alkylamino; $R_1$ and $R_2$ are independently phenyl, mono- or polysubstituted phenyl in which the substituents are substantially nonreactive towards magnesium or dialkylmagnesium compounds, or a tertiary alkyl group having the formula

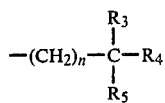

in which n is zero or 1 and $R_3$, $R_4$ and $R_5$ are independently methyl or ethyl; Y is hydrogen or a substituent which is substantially non-reactive towards magnesium and- dialkylmagnesium compounds, and m is an integer from 1 to 3;

(ii) a substance produced by reacting a compound as defined in (i) with magnesium or dialkylmagnesium compounds; or (iii) a mixture of a substance as defined in (i) or (ii) with an organoaluminum viscosity reducing agent;

wherein the mole ratio of magnesium to substance (i) and/or (ii) is at least 8.5:1.

2. A hydrocarbon solution according to claim 1 in which the viscosity reducing agent is a benzene derivative substituted at the 2- and 6- positions by tertiary alkyl groups.

3. A hydrocarbon solution according to claim 2 in which the benzene derivative is 2,6-di-tert-butylphenol.

4. A hydrocarbon solution according to claim 2 in which the benzene derivative is 2,6-di-tert-butyl-4-methylphenol.

5. A hydrocarbon solution according to claim 1 in which the viscosity reducing agent is 2,6-diphenylphenol.

6. A hydrocarbon solution according to claim 1 in which the viscosity reducing agent is 2,4,6-tri-tert-butyl aniline.

7. A hydrocarbon solution according to claim 1 in which the hydrocarbon solvent contains from 5 to 20 carbon atoms, inclusive.

8. A hydrocarbon solution according to claim 1 in which the dialkylmagnesium compound is n-butylethylmagnesium.

9. A hydrocarbon solution according to claim 1 in which the dialkylmagnesium compound is a mixture of n-butylethylmagnesium and di-n-hexylmagnesium.

10. A hydrocarbon solution according to claim 1 in which the viscosity reducing agent is a mixture of a substance as defined in (i) with an organoaluminum viscosity reducing agent.

11. A hydrocarbon solution according to claim 10 in which the organoaluminum viscosity reducing agent is a trialkylaluminum.

* * * * *